(12) United States Patent
Ban et al.

(10) Patent No.: US 11,439,536 B2
(45) Date of Patent: Sep. 13, 2022

(54) OPTICAL FILTER ON CONTACT LENS SURFACE

(71) Applicant: LUTRONIC VISION INC., Burlington, MA (US)

(72) Inventors: Dayan Ban, Waterloo (CA); Rongping Dai, Beijing (CN); Cameron Graeme Cooke, Mosman (AU); Heechul Lee, Goyang-si (KR)

(73) Assignee: LUTRONIC VISION INC., Burlington, MA (US)

( * ) Notice: Subject to any disclaimer, the term of this patent is extended or adjusted under 35 U.S.C. 154(b) by 49 days.

(21) Appl. No.: 16/766,270

(22) PCT Filed: Nov. 22, 2017

(86) PCT No.: PCT/CN2017/112311
§ 371 (c)(1),
(2) Date: May 21, 2020

(87) PCT Pub. No.: WO2019/100248
PCT Pub. Date: May 31, 2019

(65) Prior Publication Data
US 2020/0368066 A1    Nov. 26, 2020

(51) Int. Cl.
A61F 9/008    (2006.01)
A61F 9/009    (2006.01)
A61F 9/00     (2006.01)

(52) U.S. Cl.
CPC .......... *A61F 9/00812* (2013.01); *A61F 9/008* (2013.01); *A61F 9/0008* (2013.01);
(Continued)

(58) Field of Classification Search
CPC .............. A61F 9/00812; A61F 9/00823; A61F 9/008–2009/00897; A61F 9/0008;
(Continued)

(56) References Cited

U.S. PATENT DOCUMENTS 4,542,964 A    9/1985 Gilson et al.
4,644,948 A    2/1987 Lang et al.
(Continued)

FOREIGN PATENT DOCUMENTS

CN    103592709 A    2/2014
CN    104812340 A    7/2015
(Continued)

OTHER PUBLICATIONS

Marcon, N. "Is Light-Induced Fluorescence Better Than the Endoscopist's Eye?", Canadian Journal of Gastroenterology and Hepatology, vol. 13, Article ID 406459, 5 pages, 1999. https://doi.org/10.1155/1999/406459 (Year: 1999).*
(Continued)

*Primary Examiner* — Mallika D Fairchild
*Assistant Examiner* — Shreya Anjaria

(57) ABSTRACT

A contact assembly (301,400) for laser surgery may include a contact lens (402) and an optical filter (404). The contact lens (402) may be configured to be positioned in an optical path of therapeutic radiation (310) directed at an eye (100) of a patient. The optical filter (404) may be coupled to an outer surface (402A) of the contact lens (402). The optical filter (404) may be transparent to the therapeutic radiation (310) with a first wavelength and may be opaque to radiation (318) with a second wavelength different than the first wavelength.

16 Claims, 10 Drawing Sheets

(52) U.S. Cl.
CPC .......... *A61F 9/009* (2013.01); *A61F 9/00823* (2013.01); *A61F 2009/00844* (2013.01); *A61F 2009/00863* (2013.01)

(58) Field of Classification Search
CPC .................. A61F 9/009; A61F 9/00821; A61F 2009/00844; A61F 2009/00863
See application file for complete search history.

(56) References Cited

U.S. PATENT DOCUMENTS

| | | | |
|---|---|---|---|
| 4,848,894 A | 7/1989 | Buser et al. | |
| 5,549,599 A * | 8/1996 | Sumiya | A61F 9/00804 606/5 |
| 5,954,711 A | 9/1999 | Ozaki et al. | |
| 6,634,753 B1 | 10/2003 | Rozenman | |
| 7,524,060 B2 | 4/2009 | Sanchez Ramos | |
| 7,947,036 B2 | 5/2011 | Lin | |
| 9,861,275 B2 | 1/2018 | Wellhoefer | |
| 2004/0039378 A1 | 2/2004 | Lin | |
| 2006/0247608 A1* | 11/2006 | Hahn | A61F 9/008 606/5 |
| 2006/0259022 A1 | 11/2006 | Lin | |
| 2007/0004863 A1* | 1/2007 | Mentak | A61F 2/1627 525/193 |
| 2009/0069794 A1* | 3/2009 | Kurtz | A61F 9/00825 606/4 |
| 2010/0021983 A1 | 1/2010 | Vogel | |
| 2010/0149483 A1* | 6/2010 | Chiavetta, III | A61F 2/1613 351/159.63 |
| 2011/0184393 A1 | 7/2011 | Brinkmann | |
| 2012/0120365 A1* | 5/2012 | Legerton | B29D 11/00644 977/773 |
| 2012/0302862 A1 | 11/2012 | Yun et al. | |
| 2014/0364744 A1* | 12/2014 | Wellhoefer | A61F 9/009 600/407 |
| 2017/0274221 A1* | 9/2017 | Barrau | G02C 7/104 |
| 2018/0203171 A1* | 7/2018 | McPherson | G02C 7/104 |

FOREIGN PATENT DOCUMENTS

| | | |
|---|---|---|
| JP | H0713117 B2 * | 2/1995 |
| WO | 03/036834 A1 | 5/2003 |
| WO | 2010/031395 A1 | 3/2010 |

OTHER PUBLICATIONS

"Light and Vision," Hyperphysics, accessed at https://web.archive.org/web/20161202153403/http://hyperphysics.phy-astr.gsu.edu/hbase/vision/eyescal.html, archived on Dec. 2, 2016, accessed on Jun. 14, 2017, pp. 4.

International Search Report and Written Opinion for International Application No. PCT/CN2017/112311 dated Aug. 10, 2018, pp. 08.

International Search Report and Written Opinion for International Application No. PCT/US2017/43387 dated Oct. 20, 2017, pp. 10.

Misaridis, T., and Jense, J.A., "Use of Modulated Excitation Signals in Medical Ultrasound. Part I: Basic Concepts and Expected Benefits," IEEE Transactions on Ultrasonics, Ferroelectrics, and Frequency Control, vol. 52, Issue 2, pp. 177-191 (Feb. 2005).

Roegener, J., et al., "Pump-probe detection of laser-induced microbubble formation in retinal pigment epithelium cells," Journal of Biomedical Optics, vol. 9, Issue 2, pp. 367-371 (Mar./Apr. 2004).

Schlott, Kerstin et al.. "Automatic temperature controlled retinal Photocoagulalion," Journal of Biomedical Optics, vol. 17, No. 6, pp. 061223-1-061223-7 (Jun. 2012).

Varikooty, J., et al., "Measurement of the Refractive Index of Soft Contact Lenses During Wear," Eye & Contact Lens, vol. 36, No. 1, pp. 2-5 (Jan. 2010).

* cited by examiner

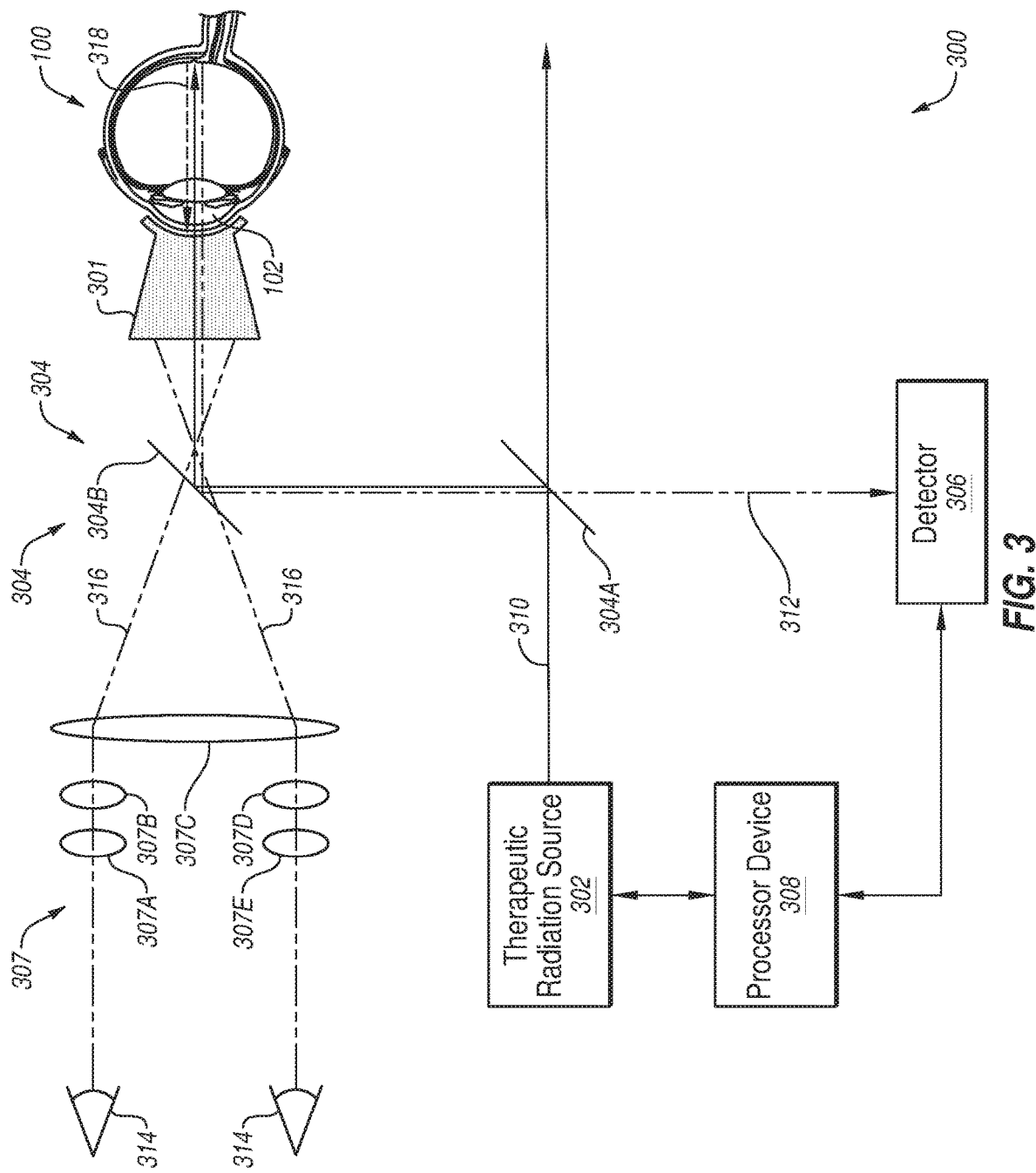

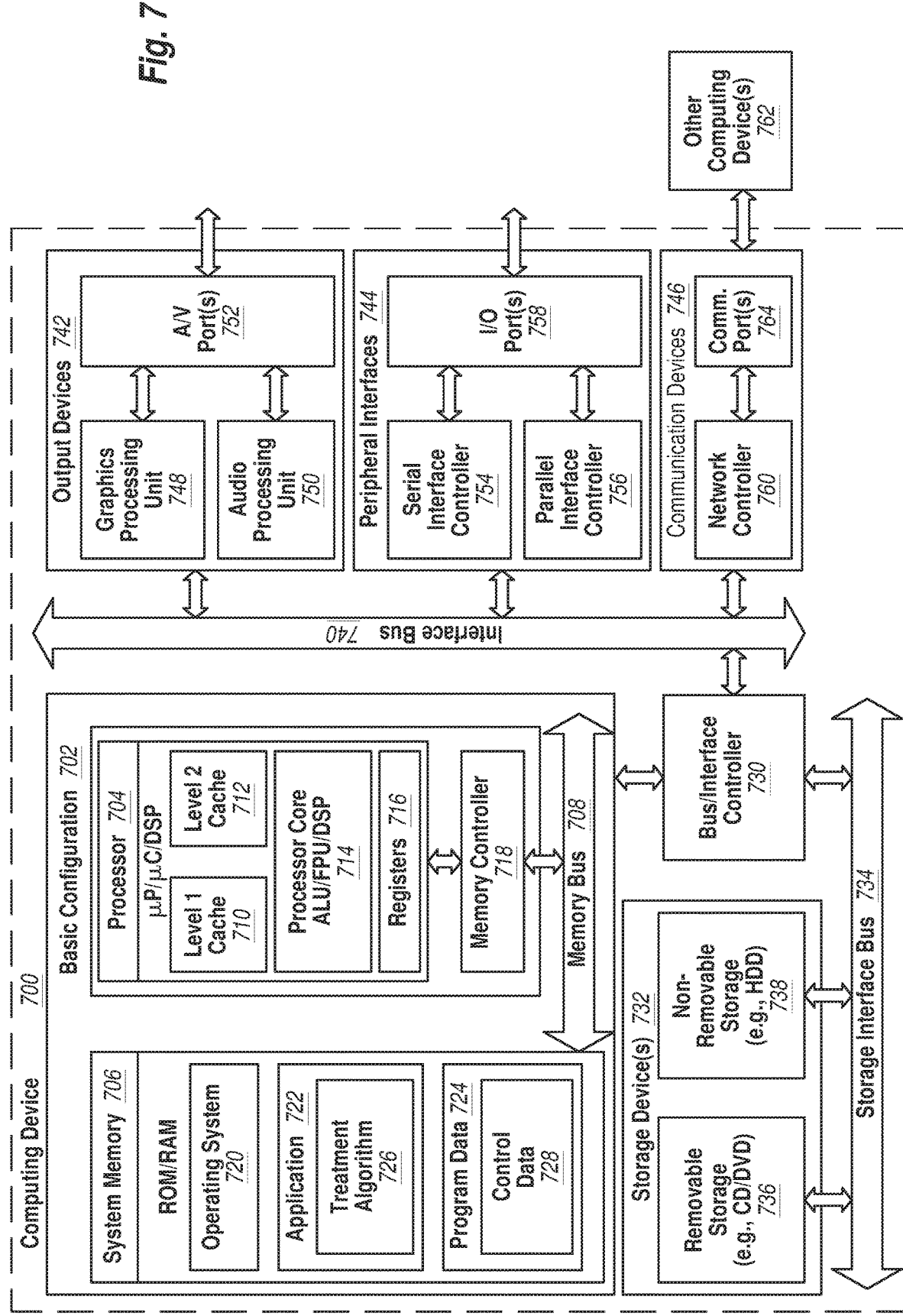

OPTICAL FILTER ON CONTACT LENS SURFACE

CROSS-REFERENCE

This patent application is section 371 nationalization of PCT Application No. PCT/CN2017/112311 filed Nov. 22, 2017, which application is incorporated herein by specific reference in its entirety.

BACKGROUND

Unless otherwise indicated herein, the materials described herein are not prior art to the claims in the present application and are not admitted to be prior art by inclusion in this section.

Therapeutic radiation may be administered to an eye of a patient to treat various conditions of the eye that may negatively affect vision. The eye of the patient may emit fluorescence radiation responsive to excitation by the therapeutic radiation. An ophthalmologist or other treatment provider may administer and monitor, e.g., through a microscope or other imaging system, treatments for multiple patients on a daily basis, including observing eyes of the patients as the eyes are exposed to the therapeutic radiation and emit fluorescence radiation. Repeated exposure of the ophthalmologist's eyes to the fluorescence radiation emitted by the eyes of the patients may be potentially hazardous to the ophthalmologist's eyes. Alternatively or additionally, the fluorescence radiation may introduce noise into measurements made during such treatments.

SUMMARY

Techniques described herein generally relate to an optical filter on a contact lens surface that may be used in therapeutic radiation treatment.

In an example embodiment, a contact lens assembly for laser surgery may include a contact lens and an optical filter. The contact lens may be configured to be positioned in an optical path of therapeutic radiation directed at an eye of a patient. The optical filter may be coupled to an outer surface of the contact lens. The optical filter may be transparent to the therapeutic radiation with a first wavelength and may be opaque to radiation with a second wavelength different than the first wavelength.

In another example embodiment, a laser-based ophthalmological surgical system may include a therapeutic radiation source, a contact lens assembly, and a head fixation assembly. The contact lens assembly may be optically coupled to the therapeutic radiation source. The head fixation assembly may be configured to position and retain a head of a patient with an eye of the patient optically aligned to the contact lens assembly to receive therethrough therapeutic radiation emitted by the therapeutic radiation source. The contact lens assembly may include a contact lens and an optical filter. The contact lens may be transparent to the therapeutic radiation. The optical filter may be coupled to an outer surface of the contact lens between the contact lens and the eye of the patient during the therapeutic treatment. The optical filter may be transparent to the therapeutic radiation and may be opaque to fluorescence radiation emitted by the eye of the patient responsive to excitation by the therapeutic radiation. The optical filter may block the fluorescence radiation from passing through the contact lens assembly.

In another example embodiment, a method to block fluorescence radiation generated in an eye of a patient responsive to illumination by therapeutic radiation emitted by a laser-based ophthalmological surgical system is described. The method may include directing the therapeutic radiation through a contact lens assembly that includes a contact lens and an optical filter coupled to an outer surface of the contact lens and into the eye of the patient. The optical filter may be transparent to the therapeutic radiation. The method may also include blocking, at the optical filter, the fluorescence radiation generated in the eye of the patient from passing through the contact lens assembly. The optical filter may be opaque to the fluorescence radiation.

In some embodiments, a contact lens assembly for laser surgery on an eye of a patient can include: a contact lens configured to be positioned in an optical path of therapeutic radiation having a first wavelength directed at the eye of the patient; and an optical filter coupled to a surface of the contact lens, the optical filter being transparent to the therapeutic radiation with the first wavelength and being opaque to radiation with a second wavelength different than the first wavelength.

In some embodiments, a laser-based ophthalmological surgical system can include: a therapeutic radiation source configured to emit therapeutic radiation; and a contact lens assembly optically coupled to the therapeutic radiation source; wherein the contact lens assembly comprises: a contact lens transparent to the therapeutic radiation; and an optical filter coupled to a surface of the contact lens, the optical filter being transparent to the therapeutic radiation and being opaque to fluorescence radiation.

In some embodiments, a method to block fluorescence radiation generated in an eye of a patient by therapeutic radiation emitted by a laser-based ophthalmological surgical system can include: directing the therapeutic radiation through a contact lens assembly that includes a contact lens and an optical filter coupled to a surface of the contact lens and into the eye of the patient, the optical filter being transparent to the therapeutic radiation and being opaque to the fluorescence radiation; and blocking the fluorescence radiation generated in the eye of the patient from passing through the contact lens assembly with the optical filter. In some aspects, the method can include removing and disposing of the contact lens assembly from the laser-based ophthalmological surgical system after therapeutic treatment of a single patient; and installing a new contact lens assembly in the laser-based ophthalmological surgical system.

In some embodiments, the optical filter includes a single layer of polymer with a polymer index of refraction $n_2$ that is different than a lens index of refraction $n_1$ of the contact lens and different than a cornea index of refraction $n_3$ of a cornea of the eye of the patient. In some aspects, the optical filter includes a single layer of polymer with a polymer index of refraction $n_2$ that is different than a lens index of refraction $n_1$ of the contact lens and different than a cornea index of refraction $n_3$ of a cornea of the eye of the patient, and the $n_2$ is about equal to $(n_1 * n_3)^{1/2}$. In some aspects, the optical filter includes a single layer of polymer with a polymer index of refraction $n_2$ that is different than a lens index of refraction $n_1$ of the contact lens and different than a cornea index of refraction $n_3$ of a cornea of the eye of the patient, and a thickness of the single layer of polymer is about equal to $3 * \lambda_2 / n_2$, where $\lambda_2$ is the second wavelength. In some aspects, the optical filter includes at least one layer of poly(hexafluoropropylene oxide) and at least one layer of phenol-formaldehyde resin.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information, as well as other features of this disclosure, will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings:

FIG. 3 is a block diagram of another example laser-based ophthalmological surgical system that may include or be optically coupled to a contact lens assembly;

FIG. 7 illustrates a block diagram of an example computing device, all arranged in accordance with at least one embodiment of the present disclosure.

DETAILED DESCRIPTION

Figure 1A:
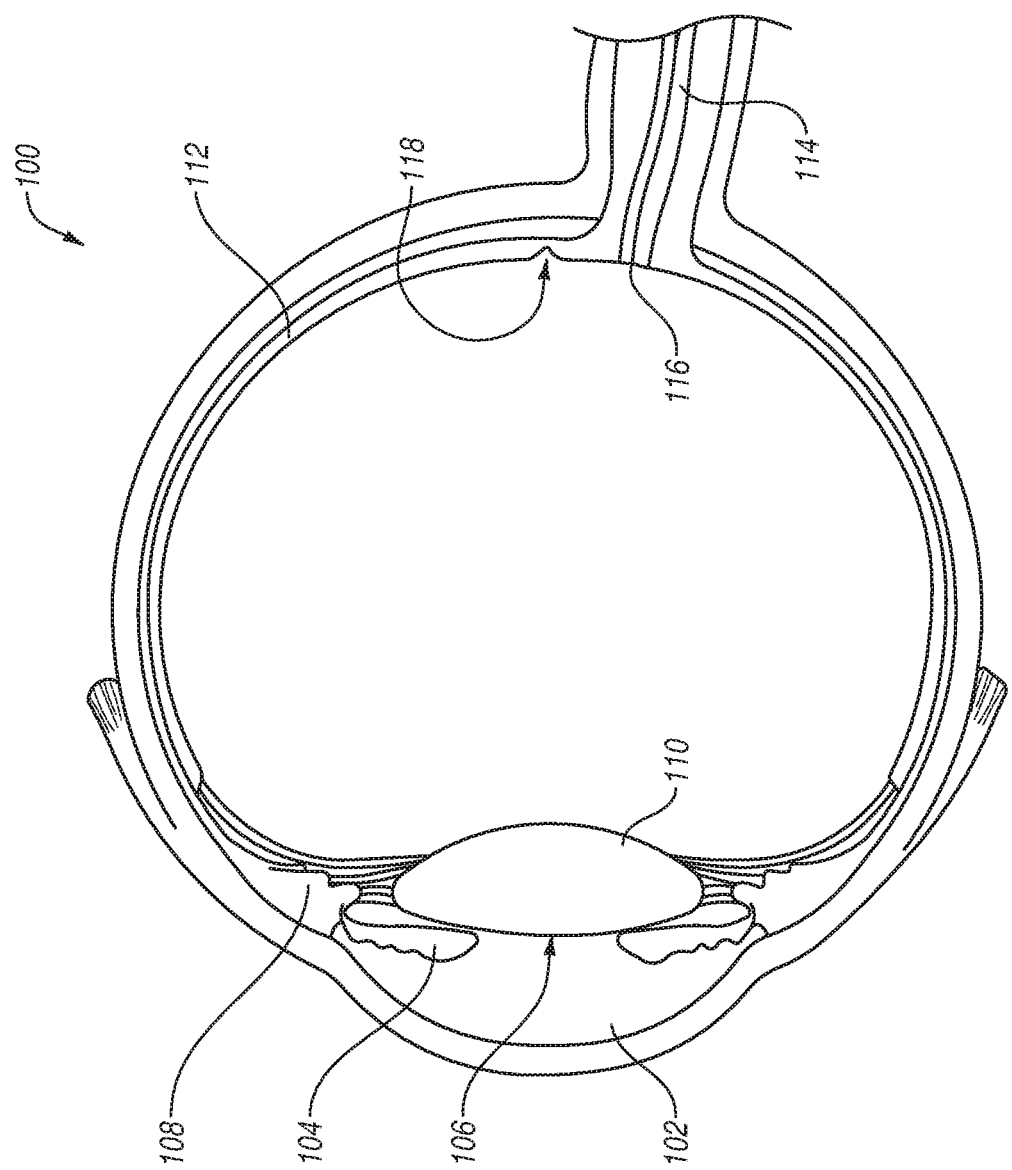
FIG. 1A is a cross-sectional view of an example human eye (hereinafter "eye")

This disclosure is generally drawn to methods, apparatus, systems, devices, and computer program products related to therapeutic radiation treatment.

A laser-based ophthalmological surgical system (hereinafter "system") may include a therapeutic radiation source. The therapeutic radiation source may be directed to an eye of a patient. The eye of the patient may emit fluorescence radiation responsive to excitation by the therapeutic radiation.

The system may be operated by an ophthalmologist or other treatment provider to provide multiple therapeutic radiation treatments per day. During each treatment, the operator may observe the corresponding eye of the corresponding patient and may be exposed to the fluorescence radiation while observing the eye. The fluorescence radiation may be potentially hazardous to the eyes of the operator of the system. Alternatively or additionally, the fluorescence radiation may introduce noise into measurements made during such treatments and it may be desirable to eliminate the noise to improve measurement accuracy.

A contact lens assembly in accordance with the present disclosure may be configured to pass therapeutic radiation to allow the eye of each patient to be treated by the system, while blocking the fluorescence radiation. Blocking the fluorescence radiation from passing through the contact lens assembly may protect the eyes of the operator of the system from exposure to the fluorescence radiation and/or may reduce noise in measurements made by the system to, e.g., improve measurement accuracy. The contact lens assembly may be removable from the system and disposable to permit use of a different contact lens assembly for each patient and for each therapeutic treatment. Each of the contact lens assemblies may be made from relatively inexpensive materials. As such, embodiments described herein may be both economical and more sanitary than reusable contact lenses that may be implemented in some other systems.

Each contact lens assembly may include a contact lens and an optical filter. The contact lens may be configured to be positioned in an optical path of therapeutic radiation directed at an eye of a patient. The optical filter may be coupled to an outer surface of the contact lens, may be transparent to the therapeutic radiation, and may be opaque to the fluorescence radiation. The optical filter may include one or more layers of polymer or other relatively inexpensive materials.

In this detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

FIG. 1A is a cross-sectional view of an example human eye (hereinafter "eye") 100, arranged in accordance with at least one embodiment described herein. The eye 100 may include a cornea 102, an iris 104, a pupil 106, a ciliary body 108, a lens 110, a retina 112, and an optic nerve 114. The retina 112 generally includes a light-sensitive layer of tissue upon which optics of the eye 100 project an image of the visual world external to the eye 100. Through a series of chemical and electrical events, nerve impulses may be triggered in response to light striking the retina 112. The nerve impulses may be processed in vision centers of the brain such that the visual world may be perceived by a person.

As illustrated in FIG. 1A, the retina 112 includes an optic disc 116, sometimes referred to as the "blind spot", and a macula 118 temporal to the optic disc 116.

Figure 1B:
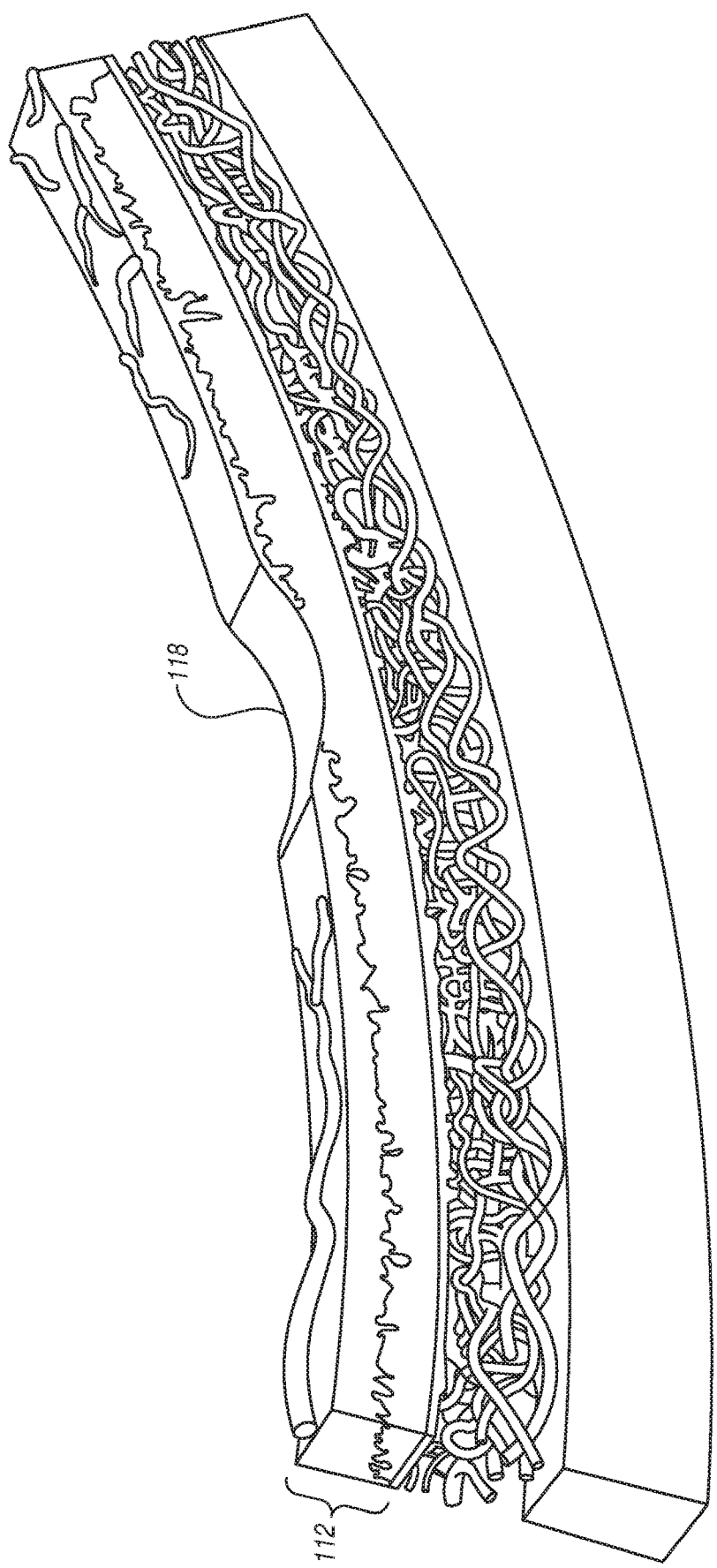
FIG. 1B is a cross-sectional perspective view of a portion of a retina and macula of FIG. 1B.

FIG. 1B is a cross-sectional perspective view of a portion of the retina 112 and the macula 118 of FIG. 1A, arranged in accordance with at least one embodiment described herein.

Figure 1C:
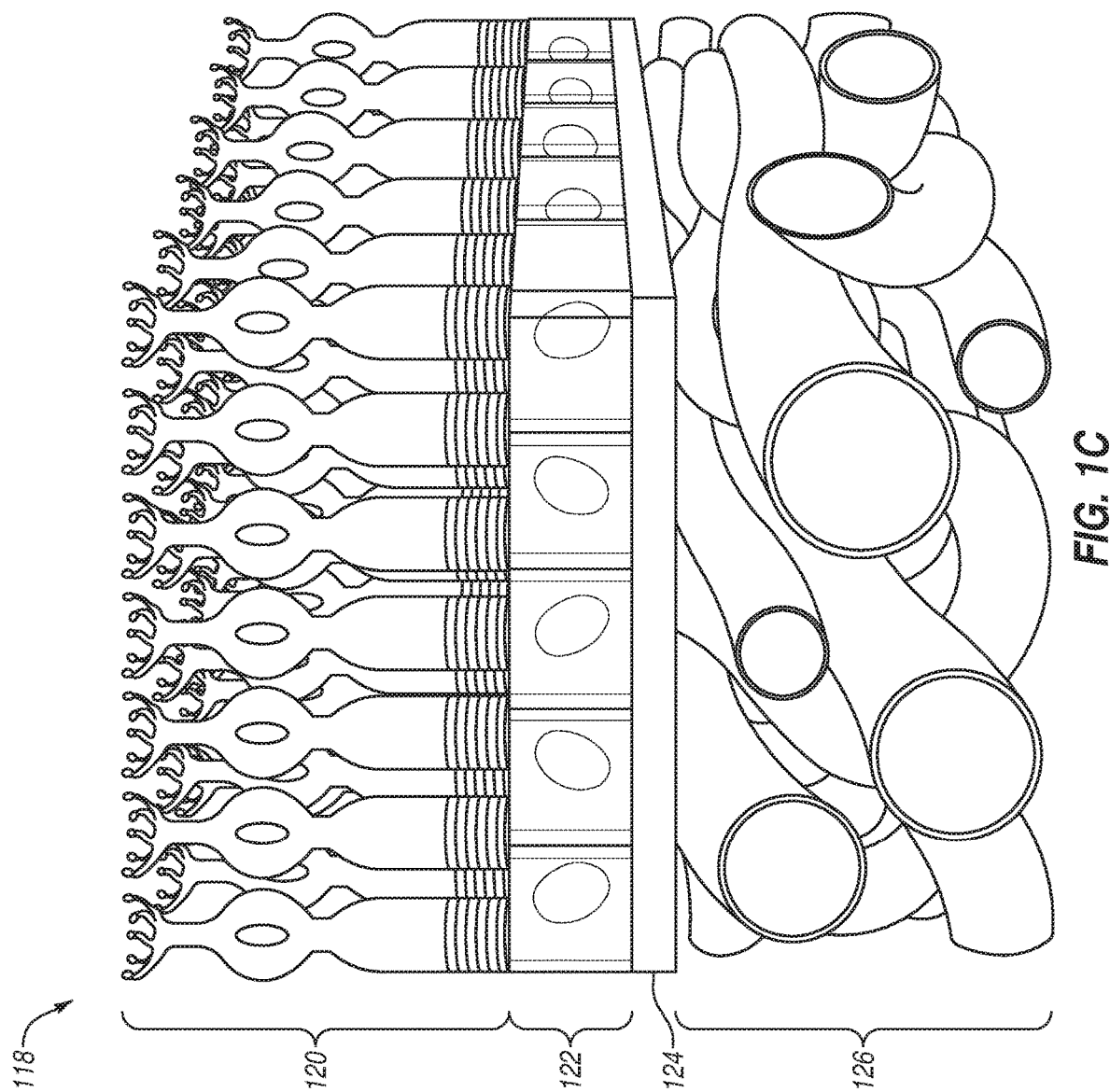
FIG. 1C is a cross-sectional perspective view of a portion of the macula of FIG. 1B.

FIG. 1C is a cross-sectional perspective view of a portion of the macula 118 of FIG. 1B, arranged in accordance with at least one embodiment described herein. FIG. 1C depicts various layers that may make up the macula 118, including photoreceptors 120, retinal pigment epithelial (RPE) cells 122, Bruch's membrane 124, and choroid 126. The macula 118 may have a relatively high concentration of photoreceptors 120 compared to the rest of the retina 112 and without blood vessels, for central and/or high resolution vision. The RPE cells 122 may nourish the photoreceptors 120 by supplying nutrients from the choroid 126 and transporting extracellular material out through the Bruch's membrane 124.

Various conditions may adversely affect vision in the eye 100. For instance, with reference to FIGS. 1A-1C, age-related macular degeneration (AMD) may involve degradation of the RPE cells 122 in the macula 118. In dry AMD, degraded RPE cells 122 may fail to transport extracellular material which may then begin to build up ("Drusen") in between the Bruch's membrane 124 and the RPE cells 122. The Drusen may interfere with the supply of nutrients to the photoreceptors 120, which can lead to vision loss. In wet AMD, new blood vessels (neovascularization) may grow from the choroid 126 and penetrate the Bruch's membrane 124 and the RPE cells 122 to supply nutrients to the photoreceptors 120. The new blood vessels may be weak and prone to bleeding and leakage, which may result in blood and protein leakages, which in turn may damage the photoreceptors 120 and fuel rapid vision loss.

Another condition that may adversely affect vision in the eye 100 may be diabetic macular edema (DME). In more detail, persons with diabetes may experience a slowing of metabolism over time, which may reduce the ability of retinal vessels to deliver enough nutrients, which in turn may induce neovascularization. Fluid leakage from the neovascularization may cause the retina 112 to swell, causing vision loss.

Another condition that may adversely affect vision in the eye 100 may be central serous chorioretinopathy (CSC). In CSC, leakage of fluid accumulates under the central macula 118, resulting in blurred or distorted vision which may progressively decline with each recurrence.

Some embodiments described herein include a contact lens assembly for use in or with a laser-based ophthalmological surgical system that includes a therapeutic radiation source configured to emit therapeutic radiation to treat AMD, DME, CSC, and/or other conditions of the eye 100. Alternatively or additionally, such a contact lens assembly may be used in other systems or devices and/or without a laser-based ophthalmological surgical system.

In general, the therapeutic radiation may be absorbed by RPE cells 122 targeted with the therapeutic radiation. Specifically, the therapeutic radiation may be absorbed by melanin or other chromophore in the RPE cells 122. The absorbed therapeutic radiation may be converted to heat, which may lead to formation of microbubbles in the RPE cells 122. The microbubbles may burst or otherwise destroy RPE cells 122. By targeting degraded RPE cells included in the RPE cells 122, the degraded RPE cells can be destroyed to prevent them from causing further damage.

According to some embodiments, such laser-based ophthalmological surgical systems may use real-time feedback to detect RPE damage and stop therapeutic radiation automatically based on the feedback prior to excessively damaging the targeted RPE cells 122. In an example embodiment, the therapeutic radiation is administered to the targeted RPE cells 122 in pulses with a pulse duration in a range from 1.6 microseconds to 1.8 microseconds. The administration of the therapeutic radiation may be periodic in some embodiments, with a pulse frequency in a range from 50 hertz (Hz) to 200 Hz (corresponding to a period in a range of 0.02 seconds to 0.005 seconds), such as about 100 Hz (corresponding to a period of 0.01 seconds). For instance, multiple therapeutic radiation pulses, each with a pulse duration of 1.7 microseconds, may be sequentially administered with a pulse frequency of 100 Hz. In other embodiments, the pulse frequency of the therapeutic radiation may be greater than 200 Hz. The administration of pulses may be terminated in response to the feedback indicating a maximum exposure to the therapeutic radiation.

The therapeutic radiation may in some embodiments be generally more effective at treating conditions of the eye at higher exposure levels, However, at a particular level of exposure (e.g., power) to the therapeutic radiation, therapeutic radiation may cause excessive damage to the eye that may result in vision loss. To avoid or reduce the likelihood of vision loss due to excessive exposure to the therapeutic radiation while permitting exposure up to a sufficiently high level to be effective, some embodiments described herein may start administration of the therapeutic radiation at a relatively low exposure that ramps up with each successive pulse until real-time feedback indicates a threshold exposure has been reached. In an example, the first pulse of therapeutic radiation may be at about 50% of a relatively high energy level, such as a maximum energy level. More generally, the first pulse may be at a relatively low energy level, and each successively administered pulse of therapeutic radiation may be increased compared to the preceding pulse. The amount of increase from pulse to pulse may be fixed or variable. For instance, in an example embodiment, the amount of increase from pulse to pulse may be fixed at 5% of the relatively high energy level.

The real-time feedback may measure exposure of the targeted RPE cells to the therapeutic radiation by measuring the formation and/or bursting of microbubbles that form on melanosomes of the targeted RPE cells and/or by measuring a temperature of the targeted area in response to exposure to the therapeutic radiation. In an example embodiment, the formation and/or bursting of the microbubbles or other measure of the exposure may be measured with optical feedback, thermal feedback, and/or acoustic feedback. In particular, the targeted RPE cells may reflect and/or emit optical and/or acoustic signals that may vary depending on the presence, absence, and/or characteristics (e.g., size, velocity) of the microbubbles and/or the targeted RPE cells may emit thermal radiation indicative of a temperature of the targeted RPE cells. Excessive exposure to the therapeutic radiation after microbubble formation and RPE damage or after reaching a target temperature could damage other retinal structures, which may lead to formation of scotoma on the retina.

The targeted RPE cells 122 and/or other portions of the eye 100 may emit fluorescence radiation in response to excitation by the therapeutic radiation. In some embodiments, the fluorescence radiation may have a center wavelength in a range from 560 to 600 nanometers (nm), or in a range from 560 to 580 nm, or at a value of about 570 nm or some other center wavelength. Alternatively or additionally, the fluorescence radiation may have a bandwidth of 100 nm or more, such as about 450 nm to 700 nm or even 400 nm to 750 nm. The fluorescence radiation and/or repeated exposure to the fluorescence radiation may be potentially hazardous to the eyes of an operator, such as an ophthalmologist or other treatment provider, that observes the eyes of the patients while the eyes of the patients are treated with the therapeutic radiation. Alternatively or additionally, the fluorescence radiation may introduce noise into measurements made during such treatments by a detector system.

Accordingly, some embodiments described herein may include contact lens assemblies generally configured to transmit therapeutic radiation and block fluorescence radiation. The contact lens assemblies may be used in or with laser-based ophthalmological surgical systems that administer therapeutic radiation to treat the eyes of patients. In some embodiments, each of the contact lens assemblies may include a low-cost one-time use device that can be disposed after a single treatment of a single patient to avoid cross-contamination between patients and/or between treatments. In some embodiments, blocking fluorescence radiation, or more generally any radiation (whether emitted as fluorescence radiation or otherwise present and propagating out of the eye 100) in one or more wavelength ranges that is/are blocked by the contact lens assemblies, may decrease background optical noise and improve performance of the detector system according to some embodiments. Alternatively or additionally, such contact lens assemblies may focus therapeutic radiation at the targeted RPE cells 122.

In use, a given contact lens assembly may be placed in contact with a patient's eye and located in an optical path between the patient's eye and a microscope or other imaging system and between the patient's eye and a therapeutic radiation source of the laser-based ophthalmological surgical system. By transmitting therapeutic radiation, each contact lens assembly may permit therapeutic radiation emitted by the therapeutic radiation source to reach a patient's eye. Alternatively or additionally, transmitting the therapeutic radiation may allow reflected therapeutic radiation to return from the patient's eye to the laser-based ophthalmological surgical system for use in detection of optical feedback to determine exposure of the patient's eye to the therapeutic radiation. In addition, by blocking fluorescence radiation emitted by the patient's eye at the contact lens assembly, an ophthalmologist or other treatment provider may observe the patient's eye through the microscope or other imaging system during treatment of the patient's eye with the therapeutic radiation and without exposing the ophthalmologist or other treatment provider to the potentially hazardous fluorescence radiation. Alternatively or additionally, blocking the fluorescence radiation at the contact lens assembly may reduce noise and thereby improve measurement accuracy of the reflected therapeutic radiation.

Figure 2A:
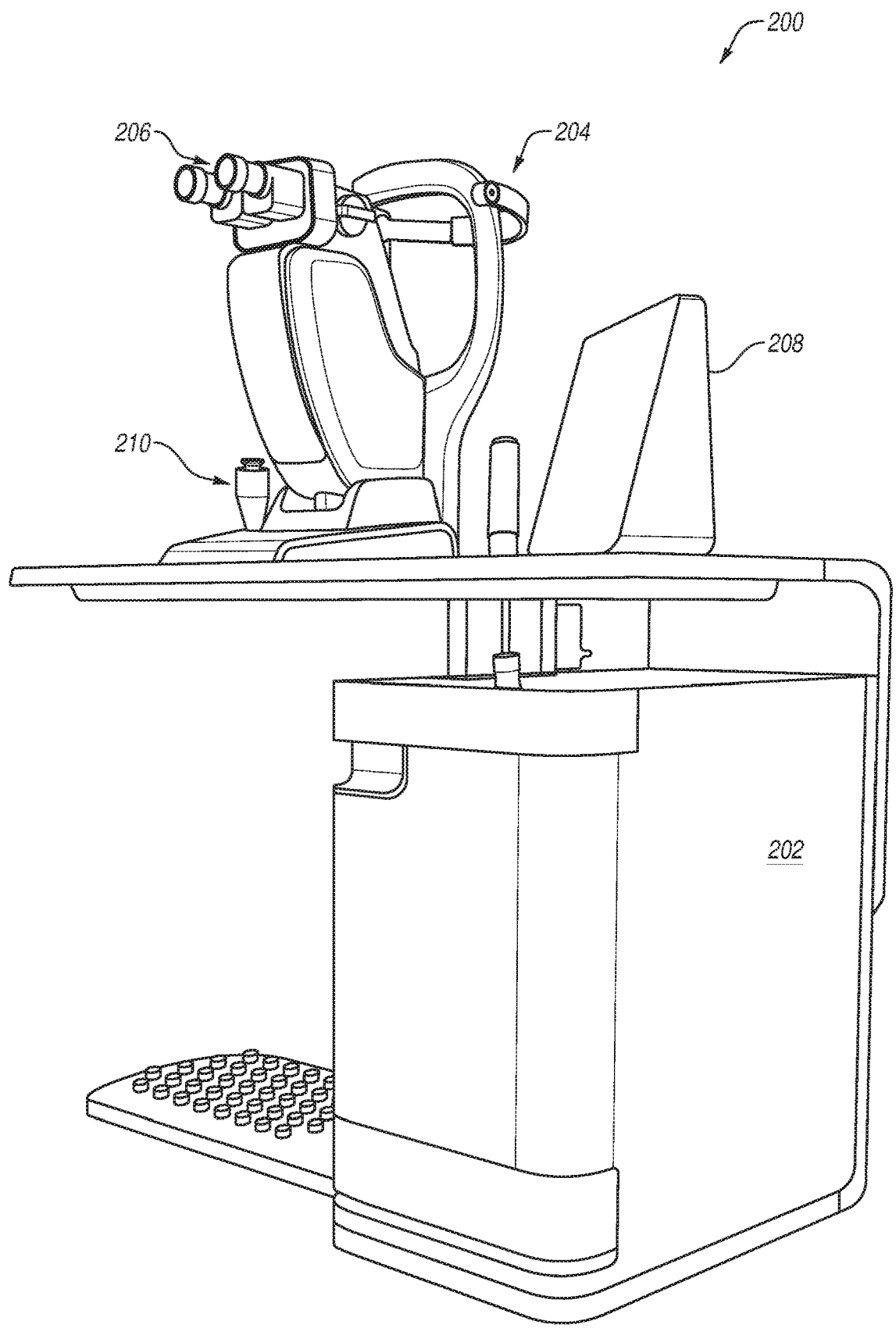
FIG. 2A is a perspective view of an example laser-based ophthalmological surgical system that may include or be optically coupled to a contact lens assembly.
Figure 2B:
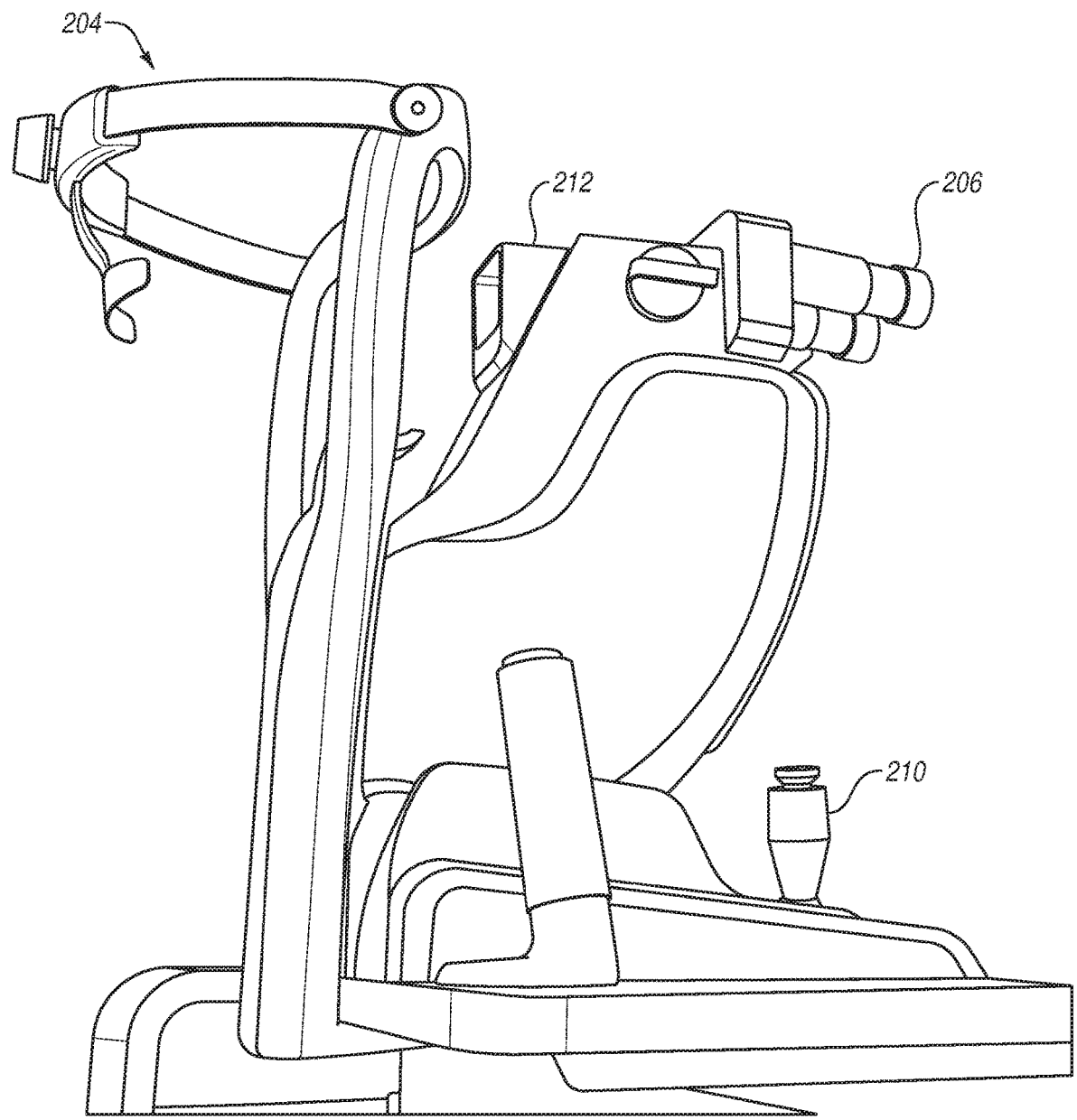
FIG. 2B is a perspective view of a portion of the laser-based ophthalmological surgical system of FIG. 2A.

FIG. 2A is a perspective view of an example laser-based ophthalmological surgical system (hereinafter "system") 200 that may include or be optically coupled to a contact lens assembly, arranged in accordance with at least one embodiment described herein. FIG. 2B is a perspective view of a portion of the system 200 of FIG. 2A, arranged in accordance with at least one embodiment described herein. As illustrated, the system 200 may include one or more of a console 202 (FIG. 2A), a head fixation assembly 204, a microscope 206, a graphical user interface (GUI) 208 (FIG. 2A), one or more input devices 210, and a patient contact lens assembly mount 212 (FIG. 2B, hereinafter "mount 212") that may selectively retain and/or be optically coupled to contact lens assemblies as described herein.

The console 202 may include a therapeutic radiation source configured to emit therapeutic radiation. The console 202 may also include one or more control systems (e.g., one or more processors, drivers, or other circuits), a cooling system, or other systems or components. The therapeutic radiation emitted by the therapeutic radiation source may have a center wavelength in a range from 440 nm to 560 nm, or in a range from 500 nm to 560 nm, or in a range from 520 nm to 540 nm, or a center wavelength of about 527 nm, or in some other range or at some other value.

The therapeutic radiation in some embodiments may be pulsed, meaning the therapeutic radiation source may emit the therapeutic radiation as discrete pulses. The pulses of therapeutic radiation may each have a pulse duration of between half a microsecond to several microseconds, such as 1.7 microseconds, and may be administered periodically in some embodiments, with a pulse frequency in a range of 50 Hz to 200 Hz, such as 100 Hz. As used herein, "pulse frequency" may refer to a frequency at which the discrete pulses of therapeutic radiation are emitted by the therapeutic radiation source, e.g., a repetition rate of the discrete pulses of therapeutic radiation. The pulses of therapeutic radiation may be substantially flat-topped or may have some other shape.

In some embodiments, the therapeutic radiation emitted by the therapeutic radiation source may have up to a maximum energy in a range from 0.5 millijoules (mJ) to 2.0 mJ, such as 1.0 mJ. The therapeutic radiation source may be controlled, e.g., by the control system or other elements of the console 202, to emit discrete pulses of the therapeutic radiation that have an energy per pulse (hereinafter "pulse energy") in a range between 0 mJ up to the maximum energy. For instance, the discrete pulses of therapeutic radiation may be sequentially ramped up beginning at a relatively low pulse energy (e.g., 50% of the maximum energy) and successively ramping up in pulse energy by a fixed or variable amount (e.g., 5% of the maximum energy) until optical, thermal, and/or acoustic feedback indicates a threshold exposure level of an eye of a patient to the therapeutic radiation has been reached.

The therapeutic radiation may be directed by one or more optical elements from the therapeutic radiation source in the console 202 up to and out through the mount 212 and a corresponding contact lens assembly to an eye of a patient during treatment with the therapeutic radiation. The one or more optical elements may be included in one or more of the console 202, the microscope 206, the mount 212, and other components of the system 200 and/or may be provided as discrete components within the system 200.

In some embodiments, a single eye of a single patient may be treated at any given time by the system 200. In these and other embodiments, at any given time, a single optical lens assembly may be selectively retained by and/or optically coupled to the mount 212 and/or the system 200. Each optical lens assembly may be discarded and replaced with a new optical lens assembly for each subsequent treatment of the patient's eye, of a different eye of the same patient, and/or of a different eye of a different patient. Alternatively, it may be possible to reuse one or more of the optical lens assemblies, e.g., for subsequent treatments of the same patient and/or after appropriate sterilization.

The head fixation assembly 204 may be configured to position and retain a head of the patient during treatment of the eye of the patient with the therapeutic radiation. For instance, the head fixation assembly 204 may be configured to position and retain the head of the patient with the eye of the patient aligned to receive the therapeutic radiation. In some embodiments in which the optical lens assembly is retained by the mount 212, the head fixation assembly 204 positioning and retaining the head of the patient may also align the eye of the patient to the mount 212 and/or the contact lens assembly.

The microscope 206 may be used by a treatment provider to observe the patient's eye during treatment. Alternatively or additionally, the microscope 206 or other component of the system 200 may include a targeting radiation source that may be optically aligned to target a same location as the therapeutic radiation. The targeting radiation source may emit targeting radiation to identify a specific location within the patient's eye currently targeted to receive therapeutic radiation. In this and other embodiments, the treatment provider may operate the input device 210, the GUI 208, and/or other elements of the system 200 to adjust the particular location within the patient's eye that is targeted by the targeting radiation and/or the therapeutic radiation.

FIG. 3 is a block diagram of another example laser-based ophthalmological surgical system (hereinafter "system") 300 that may include or be optically coupled to a contact lens assembly 301, arranged in accordance with at least one embodiment described herein. The system 300 may include or correspond to the system 200 of FIGS. 2A and 2B. The system 300 may include a therapeutic radiation source 302, one or more optical elements 304, a detector 306, and a microscope 307 or other imaging system. Alternatively or additionally, the system 300 may include a processor device 308. The contact lens assembly 301 may be included as part of the system 300 or may be considered as separate from the system 300. The detector 306 and the processor device 308 combined may form a detector system that may include or correspond to other detector systems described herein. The system 300 may include one or more other elements not depicted in FIG. 3 for simplicity.

The therapeutic radiation source 302 may be configured to emit therapeutic radiation 310 with a center wavelength within a range and/or at a value as described elsewhere herein. The therapeutic radiation 310 in some embodiments may be pulsed, meaning the therapeutic radiation source 302 may emit the therapeutic radiation 310 as discrete pulses as described elsewhere herein. The pulses of therapeutic radiation 310 may be substantially flat-topped or may have some other shape. As described elsewhere herein, the therapeutic radiation source 302 may be controlled to emit discrete pulses of the therapeutic radiation 310 that have a pulse energy in a range between 0 mJ up to the maximum energy and/or may be sequentially ramped up in pulse energy or ramped up in some other way.

The optical elements 304 may be configured to direct the therapeutic radiation 310 to the targeted area of the eye 100, and in particular to targeted RPE cells within the targeted area. Alternatively or additionally, the optical elements 304 may additionally be configured to communicatively couple the detector 306 to the targeted area of the eye 100 such that the detector 306 may receive and measure feedback 312 from the targeted area responsive to exposure to the therapeutic radiation 310. The feedback 312 may include any feedback indicative of the exposure level of the eye 100 of the patient to the therapeutic radiation 310, such as optical feedback, thermal feedback, and/or acoustic feedback as described elsewhere herein. Accordingly, the optical elements 304 may more generally be implemented as signal directing elements, whether the signals be optical, thermal, and/or acoustic. For the discussion that follows, however, it is assumed that the signals directed by the optical elements 304 are optical signals.

In some embodiments, at least a portion of the therapeutic radiation 310 may be reflected by targeted RPE cells or other portions of the eye 100. The reflected therapeutic radiation may be used as the feedback 312 in some embodiments. Alternatively or additionally, the reflected therapeutic radiation may be hazardous to eyes 314 of an ophthalmologist or other treatment provider that may operate the system 300. In these and other embodiments, the system 300 may further include a therapeutic radiation filter to block reflected therapeutic radiation from reaching the eyes 314 of the ophthalmologist or other treatment provider. In some embodiments, the therapeutic radiation filter may be included in the microscope 307 or between the microscope and the optical elements 304, or at some other location in the system 300. The therapeutic radiation filter may include a band-stop filter, such as a notch filter, centered at or near a center wavelength of the reflected therapeutic radiation.

The optical elements 304 in FIG. 3 include first and second beam directors 304A and 304B. In FIG. 3, the first and second beam directors 304A and 304B are both common to optical paths of the therapeutic radiation 310 and the feedback 312. Alternatively or additionally, the optical elements 304 may include other components not illustrated in FIG. 3, some of which may be common to both optical paths, others of which may be in the optical path of the therapeutic radiation 310 but not in the optical path of the feedback 312, and/or others of which may be in the optical path of the feedback 312 but not in the optical path of the therapeutic radiation 310.

The first beam director 304A may be configured to redirect the therapeutic radiation 310 emitted by the therapeutic radiation source 302 toward the second beam director 304B. The first beam director 304A may also be configured to pass the feedback 312 collected from the eye 100 as it travels from the second beam director 304B to the detector 306. Accordingly, the first beam director 304A may include, e.g., a beam splitter, a dichroic filter, or other suitable optical element.

The detector 306 may include any detector suitable to receive the feedback 312 and generate a signal indicative of the feedback 312 or of some parameter (e.g., intensity) of the feedback 312. The processor device 308 may be communicatively coupled to the detector 306 and/or to the therapeutic radiation source 302. The processor device 308 may be configured to receive the signal, such as a detected intensity signal, from the detector 306. Alternatively or additionally, the processor device 308 may be configured to calculate the exposure level of the targeted area of the eye 100 to the therapeutic radiation 310 based on the signal received from the detector 306 and/or based on one or more other signals or data.

In an example embodiment, the processor device 308 may control the therapeutic radiation source 302 to emit discrete pulses of the therapeutic radiation 310 at a particular pulse frequency, pulse duration, and/or pulse energy. Alternatively or additionally, the processor device 308 may be configured to turn off the therapeutic radiation source 302 responsive to the exposure level of the eye 100 of the patient reaching or exceeding a threshold exposure level.

The microscope 307 or other imaging system may be configured to present a real-time view of the eye 100 of the patient, or at least of the targeted area of the eye 100 of the patient, to the eyes 314 of the ophthalmologist or other treatment provider for observation, e.g., during treatment. For instance, the microscope 307 may include one or more lenses 307A-307E and/or other optical elements configured to direct, redirect, magnify, shape, and/or otherwise process observation radiation 316 collected from the eye 100 of the patient for viewing by the eyes 314 of the ophthalmologist or other treatment provider. The microscope 307 or other imaging system may include more or fewer lenses and/or other optical elements than are illustrated in FIG. 3 in some embodiments. Alternatively or additionally, the observation radiation 316 may include at least a portion of a broad spectrum white light reflected from the eye 100 and/or from the targeted area of the eye 100, at least a portion of the targeting radiation that is reflected from the eye 100 and/or from the targeted area of the eye 100, or other radiation that may be used to view the eye 100 and/or the targeted area of the eye 100 through the microscope 307 or other imaging system. In these and other embodiments, the second beam director 304B and/or the contact lens assembly 301 may be at least partially transparent to the observation radiation 316.

The contact lens assembly 301 may generally be located in an optical path of the therapeutic radiation 310 directed at the eye 100 of the patient. The contact lens assembly 301 may be directly coupled to the system 300 and/or may be retained in the system 300, e.g., by the mount 212 discussed elsewhere herein. Alternatively, the contact lens assembly 301 may not be directly coupled to the system 300.

In some embodiments, the contact lens assembly 301 may be in direct physical contact with the cornea 102 of the eye 100 during use of the contact lens assembly 301 and/or during treatment with the system 300. In other embodiments, the contact lens assembly 301 may be spaced apart from the eye 100 during use of the contact lens assembly 301 and/or during treatment with the system 300. The contact lens assembly 301 and other contact lens assemblies described herein may be removable, e.g., from the system 300, and disposable to permit use of a different contact lens assembly for each patient and for each therapeutic treatment.

As described in more detail elsewhere herein, the contact lens assembly 301 may generally include a contact lens and an optical filter. The contact lens of the contact lens assembly 301 may be transparent to the therapeutic radiation 310 and to fluorescence radiation 318 emitted by the eye 100, and in particular by RPE cells in the targeted area of the eye 100 and/or by other portions of the eye 100, responsive to excitation by the therapeutic radiation 310. The optical filter of the contact lens assembly 301 may be transparent to the therapeutic radiation 310. However, the optical filter of the contact lens assembly 301 may be opaque to the fluorescence radiation 318. Accordingly, the optical filter of the contact lens assembly 301 may block or substantially block the fluorescence radiation 318 from reaching the eyes 314 of the ophthalmologist or other treatment provider. Alternatively or additionally, the optical filter of the contact lens assembly 301 may block or substantially block the fluorescence radiation 318 to reduce noise and improve measurement accuracy of the feedback 312 by the detector 306.

Figure 4A:
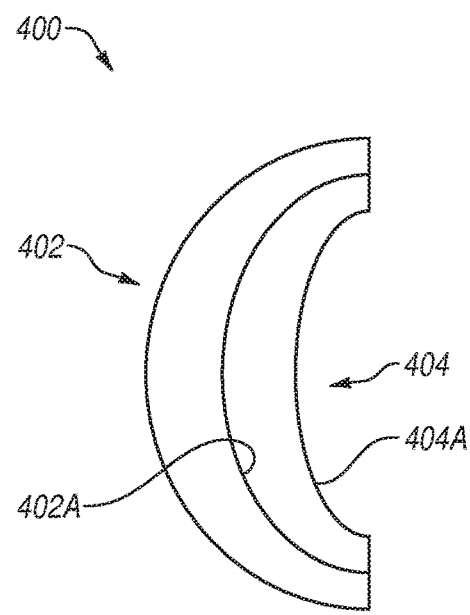
FIG. 4A illustrates an example contact lens assembly.

FIG. 4A illustrates an example contact lens assembly 400, arranged in accordance with at least one embodiment described herein. The contact lens assembly 400 may include or correspond to the contact lens assembly 301 or other contact lens assemblies described herein. The contact lens assembly 400 may include a contact lens 402 and an optical filter 404. Alternatively or additionally, the contact lens assembly 400 may further include a frame and/or more mass (e.g., as part of the contact lens 402) not depicted in FIG. 4A to provide sufficient structure for coupling to another system or device, such as the mount 212 of the system 200.

In general, the contact lens 402 may be configured to be positioned in an optical path of therapeutic radiation directed at an eye of a patient, such as an optical path of the therapeutic radiation 310. Alternatively or additionally, the contact lens 402 may be configured to be positioned in an optical path between an eye of a patient (e.g., the eye 100) and a laser-based ophthalmological surgical system (e.g., the system 200 and/or 300) configured to emit therapeutic radiation (e.g., the therapeutic radiation 310) through the contact lens assembly and into the eye of a patient.

Figure 4B:
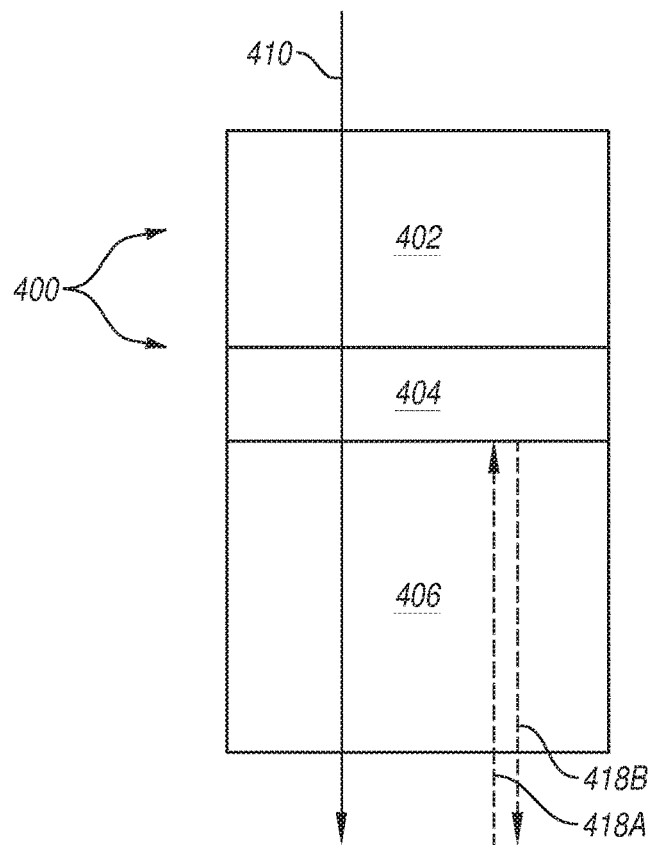
FIG. 4B includes a detail view of a portion of the contact lens assembly of FIG. 4A in use on a cornea of an eye of a patient.

In general, the optical filter 404 may be coupled to an outer surface 402A of the contact lens 402. Alternatively or additionally, the contact lens 402 may be fabricated with an integral filter function to be opaque to a desired wavelength or wavelength range, or the optical filter 404 may be coupled to a different surface of the contact lens 402 than is illustrated in FIGS. 4A and 4B. The outer surface 402A of the contact lens 402 may include a surface of the contact lens 402 that faces the eye of the patient during use of the contact lens assembly 400. Accordingly, the optical filter 404 may be located between the contact lens 402 and the eye of the patient during therapeutic treatment of the patient. Alternatively or additionally, the optical filter 404, such as an outer surface 404A of the optical filter 404, may come in direct physical contact with a cornea (e.g., the cornea 102) of the eye of the patient during therapeutic treatment of the patient with the laser-based ophthalmological surgical system. The optical filter 404 may be transparent to the therapeutic radiation (e.g., the therapeutic radiation 310) with a first wavelength and may be opaque to radiation (e.g., the fluorescence radiation 318) with a second wavelength different than the first wavelength.

The transparency and/or opacity of the optical filter 404 with respect to the first and second wavelengths may be quantified according to any suitable parameter. For instance, the optical filter 404 being transparent to the therapeutic radiation with the first wavelength may include the optical filter 404 having a transmittance of at least 50% or at least 70% or some other value with respect to the first wavelength. The optical filter 404 being opaque to radiation with the second wavelength may include the optical filter 404 having a transmittance less than 50% or less than 40% or some other value with respect to the second wavelength. While defined in terms of transmittance, in other embodiments the transparency and/or opacity of the optical filter 404 may be defined in terms of other parameters, such as reflectance, absorption, and/or other optical parameter.

FIG. 4B includes a detail view of a portion of the contact lens assembly 400 of FIG. 4A in use on a cornea 406 of an eye of a patient, arranged in accordance with at least one embodiment described herein. The cornea 406 may include or correspond to the cornea 102 described elsewhere herein. FIG. 4B additionally depicts therapeutic radiation 410 and fluorescence radiation 418A that may respectively include or correspond to the therapeutic radiation 310 and fluorescence radiation 318 described elsewhere herein.

As illustrated in FIG. 4B, the contact lens assembly 400 in general and the optical filter 404 in particular may be transparent to the therapeutic radiation 410 and opaque to the fluorescence radiation 418A. The opacity of the optical filter 404 with respect to the fluorescence radiation 418A may result from making the optical filter 404 reflective with respect to the fluorescence radiation 418A such that the fluorescence radiation 418A is reflected as reflected fluorescence radiation 418B by the optical filter 404.

The optical filter 404 may include at least one layer of polymer. For instance, the optical filter 404 may include a single layer of polymer or two or more layers of polymer. By way of example, each layer of polymer in the optical filter 404 may include at least one of poly(hexafluoropropylene oxide), poly(tetrafluoroethylene-co-hexafluoropropylene), poly(pentadecafluorooctyl acrylate), poly(octafluoropentyl acrylate), poly(methyl 3,3,3-trfluoropropyl siloxane), poly (pentafluoropropyl acrylate), poly(2-heptafluorobutoxy) ethyl acrylate, poly(chlorotrifluoroethylene), poly(2,2,3,4,4-hexafluorobutyl acrylate), poly(methyl hydro siloxane), poly (methacrylic acid) sodium salt, poly(dimethyl siloxane), poly(trifluoroethyl acrylate), poly(2-(1,1,2,2-tetrafluoroethoxy)ethyl acrylate), poly(trifluoroisopropyl methacrylate), poly(2,2,2-trifluoro-1-methylethyl methacrylate), poly(2-trifluoroethoxyethyl acrylate), poly(vinylidene fluoride), poly (2-vinylnaphthalene), poly(N-vinyl carbazole), naphthalene-formaldehyde rubber, phenol-formaldehyde resin, or poly(pentabromophenyl methacrylate).

In an example, the optical filter 404 includes a single layer of polymer deposited on the contact lens 402 and the contact lens assembly 400 is configured to be used with the optical filter 404 in direct physical contact with the cornea 406. In some embodiments, the single layer of polymer of the optical filter 404 may be deposited on the contact lens 402 by spin coating. Alternatively or additionally, a polymer index of refraction $n_2$ of the single layer of polymer and thus of the optical filter 404 may be different than a lens index of refraction $n_1$ of the contact lens 402 and different than a cornea index of refraction $n_3$ of the cornea 406.

Alternatively or additionally, the polymer index of refraction $n_2$ may be selected based on the lens index of refraction $n_1$ and the cornea index of refraction $n_3$. For instance, the polymer index of refraction $n_2$ may be selected to satisfy an equation:

$$n_2 = (n_1 * n_3)^{1/2} \qquad \text{eq. 1.}$$

In equation 1, $n_1$, $n_2$, and $n_3$ are as already defined above. As an example of an application of equation 1, the lens index of refraction $n_1$ may be 1.422, the cornea index of refraction $n_3$ may be 1.376, and the polymer index of refraction $n_2$ may be 1.399 in an example implementation.

In some embodiments in which the optical filter 404 includes a single layer of polymer, a thickness d of the single layer of polymer may be selected to satisfy another equation:

$$d = 3\lambda_1/n_2 \qquad \text{eq. 2.}$$

In equation 2, d and $n_2$ are as already defined above and $\lambda_1$ is the center wavelength of the fluorescence radiation 418A. As an example of an application of equation 2, the center wavelength $\lambda_1$ may be 570 nm, the polymer index of refraction $n_2$ may be 1.399, and the thickness d of the single layer of polymer may be 1222 nm in an example implementation.

In embodiments in which the optical filter 404 includes a single polymer layer, configuring the single polymer layer of the optical filter 404 with the polymer index of refraction $n_2$ according to equation 1 and the thickness d according to equation 2 may ensure or substantially ensure that the therapeutic radiation 410 is transmitted through the optical filter 404 and the fluorescence radiation 418A is reflected or otherwise blocked by the optical filter 404.

In other embodiments, the optical filter 404 may include multiple layers of polymer where at least two of the layers have a different index of refraction or other parameter than the other. For instance, the multiple layers of polymer may include at least one layer of poly(hexafluoropropylene oxide) and at least one layer of phenol-formaldehyde resin.

Figure 5A:
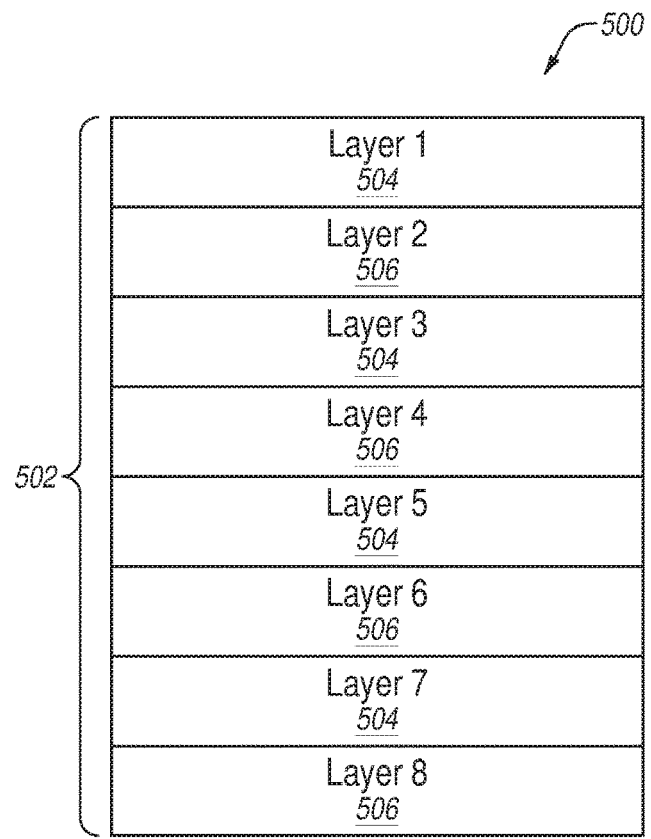
FIG. 5A illustrates an example optical filter that includes multiple layers of polymer.

FIG. 5A illustrates an example optical filter 500 that includes multiple layers 502 of polymer, arranged in accordance with at least one embodiment described herein. The optical filter 500 may include or correspond to the optical filter 404 or other optical filters described herein.

The layers 502 of the optical filter 500 include first layers 504 of a first material that alternate with second layers 506 of a second material. Each of the first layers 504 may include poly(hexafluoropropylene oxide) while each of the second layers 506 may include phenol-formaldehyde resin. Accordingly, each of the first layers 504 may have an index of refraction of 1.3 while each of the second layers 506 may have an index of refraction of 1.7.

Alternatively or additionally, each of the first layers 504 and each of the second layers may have a thickness of 570 nm, or more generally a thickness equal to a center wavelength of the fluorescence radiation (e.g., fluorescence radiation 318 and 418A) in some embodiments. In other embodiments, each of the first layers 504 may have a different thickness than each of the second layers 506, some of the first layers 504 may have a different thickness than others of the first layers 504, and/or some of the second layers 506 may have a different thickness than others of the second layers 506.

Figure 5B:
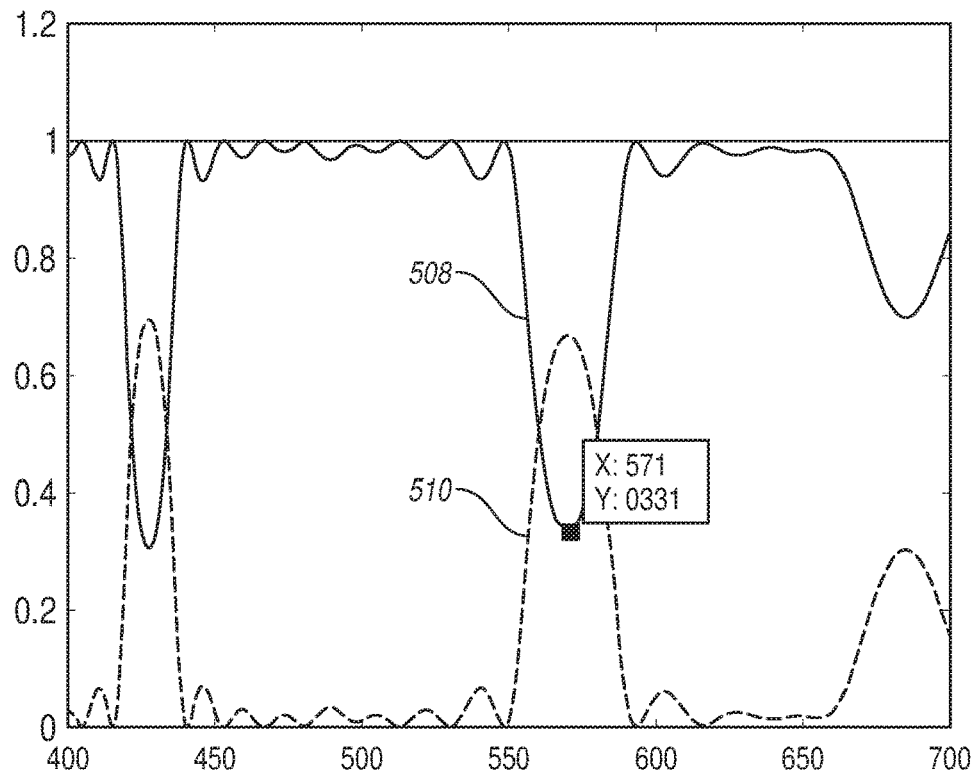
FIG. 5B includes a graphical representation of simulated performance as a function of wavelength of the optical filter of FIG. 5A.

FIG. 5B includes a graphical representation of simulated performance as a function of wavelength of the optical filter 500 of FIG. 5A, arranged in accordance with at least one embodiment described herein. The simulated performance includes a first curve 508 that represents transmittance of the optical filter 500 as a function of wavelength (in nanometers) and a second curve 510 that represents reflectance of the optical filter 500 as a function of wavelength (in nanometers). It can be seen that the first and second curves 508 and 510 are generally the inverse of each other.

With continued reference to FIGS. 5A and 5B, the transmittance of the optical filter 500 at a wavelength of 527 nm (corresponding to the center wavelength of the therapeutic radiation in some embodiments) is at least 95% while the reflectance at the wavelength of 527 nm is less than 5%. Further, the transmittance of the optical filter 500 at a wavelength of 570 nm (corresponding to the center wavelength of the fluorescence radiation in some embodiments) is less than 40% while the reflectance at the wavelength of 570 nm is more than 60%. Thus, the optical filter 500 is one example of an optical filter with multiple layers of polymer that may be implemented in a contact lens assembly to transmit therapeutic radiation with a center wavelength of 527 nm while blocking fluorescence radiation with a center wavelength of 570 nm. The specific layers 502, their indexes of refraction, and their thickness may be modified from that described with respect to FIG. 5A depending on the center wavelengths of the radiation that is desired to pass through (e.g., therapeutic radiation) and of the radiation that is desired to be blocked (e.g., the fluorescence radiation).

The polymer layer or layers included in optical filters described herein may be relatively inexpensive with suitable refractive indices to reduce or maintain manufacturing costs at a relatively low level. Examples of such polymer layers are described elsewhere herein. Such polymer layers may have refractive indices in a range from, e.g., 1.3 to 1.7, or less than 1.3 or more than 1.7.

Alternatively or additionally, the polymer layer or layers may be configured to maintain at least a threshold level of transparency with respect to the therapeutic radiation with the first wavelength for at least a threshold number of ablations of the therapeutic radiation. For instance, the threshold number of ablations may be at least 100, or at least 350. If a treatment involves more treatments than the threshold number of ablations for which the polymer layer or layers are rated, the contact lens assembly to which the polymer layer or layers belong may be replaced during treatment.

Figure 6:
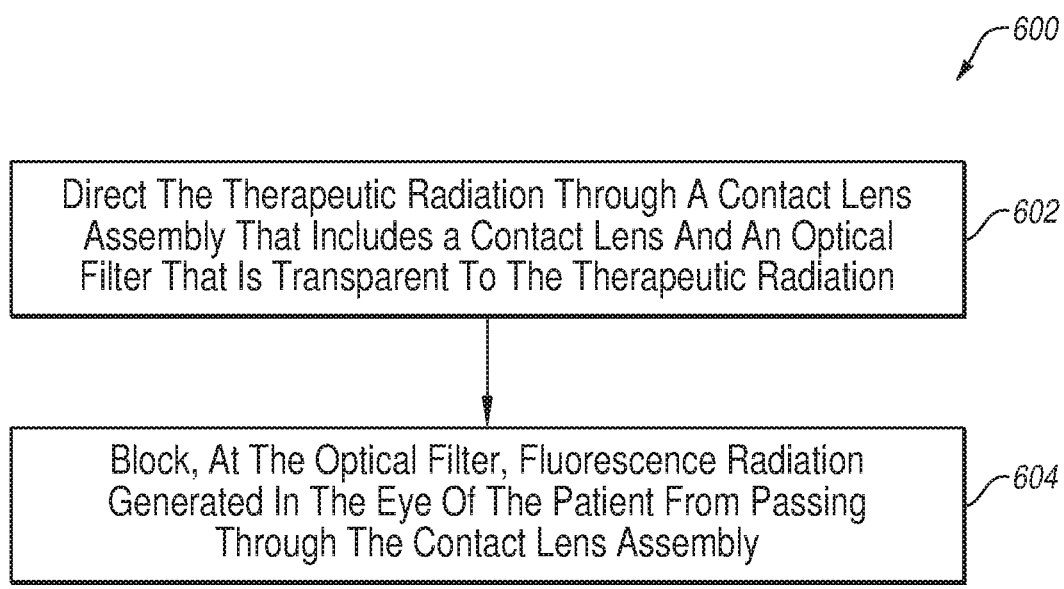
FIG. 6 illustrates a flow diagram of an example method to block fluorescence radiation.

FIG. 6 illustrates a flow diagram of an example method 600 to block fluorescence radiation, arranged in accordance with at least some embodiments described herein. The fluorescence radiation may be generated in an eye of a patient responsive to illumination by therapeutic radiation emitted by a laser-based ophthalmological surgical system. The fluorescence radiation may be blocked from an eye of an operator of the laser-based ophthalmological surgical system and/or from a detector system of the laser-based ophthalmological surgical system. The operator may include an ophthalmologist or other treatment provider. The laser-based ophthalmological surgical system may include either of the systems 200 or 300 or other laser-based ophthalmological surgical system.

The method 600 may be performed, in whole or in part, in the systems 200, 300 and/or in other systems and configurations. Alternatively or additionally, the method 600 may be implemented by a processor device that performs or controls performance of one or more of the operations of the method 600. For instance, a computer (such as the computing device 700 of FIG. 7) or other processor device may be communicatively coupled to the system 200 or 300 and may execute software or other computer-readable instructions accessible to the computer, e.g., stored on a non-transitory computer-readable medium accessible to the computer, to perform or control the system 200 or 300 to perform the method 600 of FIG. 6.

The method 600 may include one or more of blocks 602 and/or 604. Although illustrated as discrete blocks, various blocks may be divided into additional blocks, supplemented with additional blocks, combined into fewer blocks, or eliminated, depending on the particular implementation. The method 600 may begin at block 602.

In block 602 ("Direct The Therapeutic Radiation Through A Contact Lens Assembly That Includes a Contact Lens And An Optical Filter That Is Transparent To The Therapeutic Radiation"), the therapeutic radiation may be directed through the contact lens assembly into the eye of the patient. The therapeutic radiation may be directed through the contact lens assembly and into the eye of the patient by one or more optical elements, such as one or more of the optical elements 304 of the system 300.

The contact lens assembly may include a contact lens and an optical filter coupled to an outer surface of the contact lens and may include or correspond to the contact lens assembly 301, 400 or other contact lens assemblies described herein. The optical filter may be transparent to the therapeutic radiation. In these and other embodiments, directing the therapeutic radiation through the contact lens assembly may include directing the therapeutic radiation through the optical filter that has a transmittance of at least 50% or at least 70% with respect to a center wavelength of the therapeutic radiation. Block 602 may be followed by block 604.

In block 604 ("Block, At The Optical Filter, Fluorescence Radiation Generated In The Eye Of The Patient From Passing Through The Contact Lens Assembly"), the fluorescence radiation generated in the eye of the patient responsive to illumination by the therapeutic radiation may be blocked at the optical filter. The optical filter may be opaque to the fluorescence radiation. In these and other embodiments, blocking the fluorescence radiation from passing through the contact lens assembly may include blocking the fluorescence radiation at the optical filter that has a transmittance of less than 50% or less than 40% with respect to a center wavelength of the fluorescence radiation.

For this and other procedures and methods disclosed herein, the functions or operations performed in the processes and methods may be implemented in differing order. Furthermore, the outlined operations are only provided as examples, and some of the operations may be optional, combined into fewer operations, supplemented with other operations, or expanded into additional operations without detracting from the disclosed embodiments.

For instance, the method 600 may further include positioning the eye of the patient and/or the cornea of the eye of the patient in direct physical contact with the optical filter of the contact lens assembly.

In an embodiment, the method 600 may further include forming the contact lens assembly by depositing at least one layer of polymer as the optical filter on the outer surface of the contact lens. Alternatively or additionally, the method 600 may further include removing and disposing of the contact lens assembly from the laser-based ophthalmological surgical system after therapeutic treatment of a single patient. Alternatively or additionally, the method 600 may further include installing a new contact lens assembly in the laser-based ophthalmological surgical system for therapeutic treatment of a different patient with the laser-based ophthalmological surgical system.

Alternatively or additionally, embodiments described herein may include methods of treating a patient and/or methods of operating a treatment device such as any of the laser-based ophthalmological surgical systems described herein. Such methods may include supporting a contact lens assembly on the eye of a patient. The contact lens assembly may include any of the contact lens assemblies described herein. Such methods may alternatively or additionally include directing therapeutic radiation through the contact lens assembly into the eye of the patient. Such methods may alternatively or additionally include blocking, at the contact lens assembly, fluorescence radiation generated in the eye of the patient from passing through the contact lens assembly.

FIG. 7 illustrates a block diagram of an example computing device 700, in accordance with at least one embodiment of the present disclosure. The computing device 700 may be used in some embodiments to perform or control performance of one or more of the methods and/or operations described herein. For instance, the computing device may be communicatively coupled to and/or included in the system 200 or 300 to perform or control performance of the method 600 of FIG. 6. In a basic configuration 702, the computing device 700 typically includes one or more processors 704 and a system memory 706. A memory bus 708 may be used for communicating between the processor 704 and the system memory 706.

Depending on the desired configuration, the processor 704 may be of any type including a microprocessor (μP), a microcontroller (μC), a digital signal processor (DSP), or any combination thereof. The processor 704 may include one or more levels of caching, such as a level one cache 710 and a level two cache 712, a processor core 714, and registers 716. The processor core 714 may include an arithmetic logic unit (ALU), a floating point unit (FPU), a digital signal processing core (DSP Core), or any combination thereof. An example memory controller 718 may also be used with the processor 704, or in some implementations, the memory controller 718 may be an internal part of the processor 704.

Depending on the desired configuration, the system memory 706 may be of any type, such as volatile memory (such as RAM), non-volatile memory (such as ROM, flash memory, or the like), or any combination thereof. The system memory 706 may include an operating system 720, one or more applications 722, and program data 724. The application 722 may include treatment algorithm 726 that is arranged to control a laser-based ophthalmological surgical system to treat patients with therapeutic radiation. The program data 724 may include control data 728 such as bias values to bias the therapeutic radiation source, pulse repetition rates, pulse durations, pulse train repetition rates, pulse train durations, and/or other data that may be used to control aspects of the therapeutic radiation emitted by the system 200 or 300 or other laser-based ophthalmological surgical systems described herein. In some embodiments, the application 722 may be arranged to operate with the program data 724 on the operating system 720 to perform one or more of the methods and/or operations described herein, including those described with respect to FIG. 6.

The computing device 700 may include additional features or functionality, and additional interfaces to facilitate communications between the basic configuration 702 and any other devices and interfaces. For example, a bus/interface controller 730 may be used to facilitate communications between the basic configuration 702 and one or more data storage devices 732 via a storage interface bus 734. The data storage devices 732 may include removable storage devices 736, non-removable storage devices 738, or a combination thereof. Examples of removable storage and non-removable storage devices include magnetic disk devices such as flexible disk drives and hard-disk drives (HDDs), optical disk drives such as compact disk (CD) drives or digital versatile disk (DVD) drives, solid state drives (SSDs), and tape drives to name a few. Example computer storage media may include volatile and nonvolatile, removable and non-removable media implemented in any method or technology for storage of information, such as computer-readable instructions, data structures, program modules, or other data.

The system memory 706, the removable storage devices 736, and the non-removable storage devices 738 are examples of computer storage media. Computer storage media includes, but is not limited to, RAM, ROM, EEPROM, flash memory or other memory technology, CD-ROM, digital versatile disks (DVDs) or other optical storage, magnetic cassettes, magnetic tape, magnetic disk storage or other magnetic storage devices, or any other medium which may be used to store the desired information and which may be accessed by the computing device 700. Any such computer storage media may be part of the computing device 700.

The computing device 700 may also include an interface bus 740 for facilitating communication from various interface devices (e.g., output devices 742, peripheral interfaces 744, and communication devices 746) to the basic configuration 702 via the bus/interface controller 730. The output devices 742 include a graphics processing unit 748 and an audio processing unit 750, which may be configured to communicate to various external devices such as a display or speakers via one or more A/V ports 752. The peripheral interfaces 744 include a serial interface controller 754 or a parallel interface controller 756, which may be configured to communicate with external devices such as input devices (e.g., keyboard, mouse, pen, voice input device, touch input device, and/or others), sensors, or other peripheral devices (e.g., printer, scanner, and/or others) via one or more I/O ports 758. The communication devices 746 include a network controller 760, which may be arranged to facilitate communications with one or more other computing devices 762 over a network communication link via one or more communication ports 764.

The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that includes one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term "computer-readable media" as used herein may include both storage media and communication media.

The computing device 700 may be implemented as a portion of a small-form factor portable (or mobile) electronic device such as a cell phone, a personal data assistant (PDA), a personal media player device, a wireless web-watch device, a personal headset device, an application-specific device, or a hybrid device that include any of the above functions. The computing device 700 may also be implemented as a personal computer including both laptop computer and non-laptop computer configurations.

The present disclosure is not to be limited in terms of the particular embodiments described herein, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of this disclosure. It is also to be understood that the terminology used herein is for the purpose of describing particular embodiments only, and is not intended to be limiting.

The present disclosure is not to be limited in terms of the particular embodiments described herein, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of this disclosure. Also, the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that include A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that include A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

For any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, and/or others. As a non-limiting example, each range discussed herein can be readily broken down into a lower third, middle third and upper third, etc. All language such as "up to," "at least," and the like include the number recited and refer to ranges which can be subsequently broken down into sub ranges as discussed above. Finally, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, various embodiments of the present disclosure have been described herein for purposes of illustration, and various modifications may be made without departing from the scope and spirit of the present disclosure. Accordingly, the various embodiments disclosed herein are not intended to be limiting.

What is claimed is:

1. A contact lens assembly for laser surgery on an eye of a patient,
the contact lens assembly comprising:
a contact lens configured to be positioned in an optical path of therapeutic radiation having a first wavelength directed at the eye of the patient; and
an optical filter coupled to a surface of the contact lens, the optical filter being transparent to the therapeutic radiation with the first wavelength and being opaque to radiation with a second wavelength different than the first wavelength,
wherein the radiation with the second wavelength includes fluorescence radiation and the second wavelength is longer than the first wavelength, and
wherein the optical filter includes a single layer of polymer with a polymer index of refraction $n_2$ that is different than a lens index of refraction $n_1$ of the contact lens and different than a cornea index of refraction $n_3$ of a cornea of the eye of the patient, and the $n_2$ is equal to $(n_1 * n_3)^{1/2}$.

2. The contact lens assembly of claim 1, wherein:
the optical filter has a transmittance of at least 50% with respect to the first wavelength; and
the optical filter has a transmittance less than 50% with respect to the second wavelength.

3. The contact lens assembly of claim 1, wherein the fluorescence radiation has a center wavelength in a range from 560 to 580 nanometers.

4. The contact lens assembly of claim 1, wherein the therapeutic radiation with the first wavelength includes therapeutic radiation with a center wavelength in a range from 520 to 540 nanometers.

5. The contact lens assembly of claim 1, wherein a thickness of the single layer of polymer is equal to $3*\lambda_2/n_2$, where $\lambda_2$ is the second wavelength.

6. The contact lens assembly of claim 1, wherein optical filter includes at least one of poly(hexafluoropropylene oxide) and phenol-formaldehyde resin.

7. The contact lens assembly of claim 1, wherein the optical filter includes at least one of:
poly(hexafluoropropylene oxide), poly(tetrafluoroethylene-co-hexafluoropropylene), poly(pentadecafluorooctyl acrylate), poly(octafluoropentyl acrylate), poly(methyl 3,3,3-trfluoropropyl siloxane), poly(pentafluoropropyl acrylate), poly(-heptafluorobutoxy) ethyl acrylate, poly(chlorotrifluoroethylene), poly(2,2,3,4,4-hexafluorobutyl acrylate), poly(methyl hydro siloxane), poly(methacrylic acid) sodium salt, poly(dimethyl siloxane), poly(trifluoroethyl acrylate), poly(2-(1,1,2,2-tetrafluoroethoxy)ethyl acrylate), poly(trifluoroisopropyl methacrylate), poly(2,2,2-trifluoro-1-methylethyl methacrylate), poly(-trifluoroethoxyethyl acrylate), poly(vinylidene fluoride), poly(-vinylnaphthalene), poly(N-vinyl carbazole), naphthalene-formaldehyde rubber, phenol-formaldehyde resin, or poly(pentabromophenyl methacrylate).

8. A method to block fluorescence radiation generated in an eye of a patient by therapeutic radiation emitted by a laser-based ophthalmological surgical system, the method comprising:
directing the therapeutic radiation through the optical filter of the contact lens assembly of claim 1 and into the eye of the patient; and
blocking, at the optical filter, the fluorescence radiation generated in the eye of the patient from passing through the contact lens assembly.

9. A laser-based ophthalmological surgical system comprising:
a therapeutic radiation source configured to emit therapeutic radiation; and
a contact lens assembly optically coupled to the therapeutic radiation source, wherein the contact lens assembly comprises:
a contact lens transparent to the therapeutic radiation; and
an optical filter coupled to a surface of the contact lens, the optical filter being transparent to the therapeutic radiation and being opaque to fluorescence radiation, wherein a wavelength of the fluorescence radiation is longer than a wavelength of the therapeutic radiation, and wherein the optical filter includes a single layer of polymer with a polymer index of refraction $n_2$ that is different than a lens index of refraction $n_1$ of the contact lens and different than a cornea index of refraction n3 of a cornea of the eye of the patient, and the $n_2$ is equal to $(n_1 * n_3)^{1/2}$.

10. The laser-based ophthalmological surgical system of claim 9, further comprising a contact lens assembly mount configured to selectively retain the contact lens assembly in the laser-based ophthalmological surgical system, wherein the contact lens assembly is disposable and removable.

11. The laser-based ophthalmological surgical system of claim 9, wherein:
   the optical filter has a transmittance of at least 50% with respect to a center wavelength of the therapeutic radiation; and
   the optical filter has a transmittance less than 50% with respect to a center wavelength of the fluorescence radiation.

12. The laser-based ophthalmological surgical system of claim 9, wherein a thickness of the single layer of polymer is equal to $3*\lambda_1/n_2$, where $\lambda_1$ is a center wavelength of the fluorescence radiation.

13. A method to block fluorescence radiation generated in an eye of a patient by therapeutic radiation emitted by a laser-based ophthalmological surgical system, the method comprising:
   directing the therapeutic radiation through a contact lens assembly that includes a contact lens and an optical filter coupled to a surface of the contact lens and into the eye of the patient, the optical filter being transparent to the therapeutic radiation and being opaque to the fluorescence radiation; and
   blocking the fluorescence radiation generated in the eye of the patient from passing through the contact lens assembly with the optical filter,
   wherein a wavelength of the fluorescence radiation is longer than a wavelength of the therapeutic radiation, and
   wherein the optical filter includes a single layer of polymer with a polymer index of refraction $n_2$ that is different than a lens index of refraction $n_1$ of the contact lens and different than a cornea index of refraction $n_3$ of a cornea of the eye of the patient, and the $n_2$ is equal to $(n_1 * n_3)^{1/2}$.

14. The method of claim 13, further comprising positioning the eye of the patient in direct physical contact with the optical filter of the contact lens assembly.

15. The method of claim 13, wherein the optical filter has a transmittance of at least 50% with respect to a center wavelength of the therapeutic radiation and a transmittance of less than 50% with respect to a center wavelength of the fluorescence radiation.

16. The method of claim 13, further comprising:
   removing and disposing of the contact lens assembly from the laser-based ophthalmological surgical system after therapeutic treatment of a single patient; and
   installing a new contact lens assembly in the laser-based ophthalmological surgical system.

\* \* \* \* \*